United States Patent [19]
Frantzen

[11] Patent Number: 5,718,713
[45] Date of Patent: Feb. 17, 1998

[54] SURGICAL STENT HAVING A STREAMLINED CONTOUR

[75] Inventor: John J. Frantzen, Copperopolis, Calif.

[73] Assignee: Global Therapeutics, Inc., Broomfield, Colo.

[21] Appl. No.: 839,434

[22] Filed: Apr. 10, 1997

[51] Int. Cl.⁶ .................................................... A61F 2/04
[52] U.S. Cl. ................... 606/198; 606/191; 606/194; 623/1; 623/12
[58] Field of Search .................... 606/191, 194, 606/195, 198; 623/1, 12

[56] References Cited

U.S. PATENT DOCUMENTS

| | | | |
|---|---|---|---|
| 5,133,732 | 7/1992 | Wiktor | 606/195 |
| 5,139,480 | 8/1992 | Hickle et al. | 604/8 |
| 5,195,984 | 3/1993 | Schatz | 606/195 |
| 5,242,399 | 9/1993 | Lau et al. | 604/104 |
| 5,314,444 | 5/1994 | Gianturco | 606/195 |
| 5,421,955 | 6/1995 | Lau et al. | 216/48 |
| 5,425,739 | 6/1995 | Jessen | 606/155 |
| 5,441,515 | 8/1995 | Khosravi et al. | 606/194 |
| 5,443,477 | 8/1995 | Marin et al. | 606/198 |
| 5,494,029 | 2/1996 | Lane et al. | 128/207.15 |
| 5,496,277 | 3/1996 | Termin et al. | 604/104 |
| 5,507,767 | 4/1996 | Maeda et al. | 606/198 |
| 5,507,771 | 4/1996 | Gianturco | 606/198 |
| 5,514,154 | 5/1996 | Lau et al. | 606/195 |
| 5,522,882 | 6/1996 | Gaterud et al. | 623/1 |
| 5,531,741 | 7/1996 | Barbacci | 606/15 |
| 5,549,662 | 8/1996 | Fordenbacher | 623/1 |
| 5,603,721 | 2/1997 | Lau et al. | 606/195 |

FOREIGN PATENT DOCUMENTS

| | | | |
|---|---|---|---|
| 95302708 | 11/1995 | European Pat. Off. | A61B 19/00 |

*Primary Examiner*—Michael Buiz
*Assistant Examiner*—David O. Reip
*Attorney, Agent, or Firm*—Bradley P. Heisler

[57] ABSTRACT

A surgical stent 10 is provided which is formed of a plurality of stent segments 40 having a streamlined contour. Each stent segment 40 includes an outer surface 42 spaced from an inner surface 44. The inner surface 44 is bordered by inner edges 54, 56 and the outer surface 42 is bordered by outer edges 50, 52. The outer edges 50, 52 have a contour defined by outer curves 64, 66 and the inner edges 54, 56 have a contour defined by inner curves 60, 62. Radii of curvature for the inner curves 70, 72 are greater than radii of curvature for the outer curves 64, 66. The inner surface 44 is thus streamlined for passage of blood/bodily fluid B adjacent the inner surface 44 and the outer surface 42 is particularly configured for maximum adherence without irritation to an inner surface S of a body lumen L, such as an artery. The surfaces 42, 44 of the stent segment 40 are provided with a surface finish of sufficient smoothness to further enhance blood/fluid flow B adjacent the stent segment 40 and to minimize irritation of tissues forming the inner surface S of the body lumen L in which the surgical stent 10 is implanted.

19 Claims, 3 Drawing Sheets

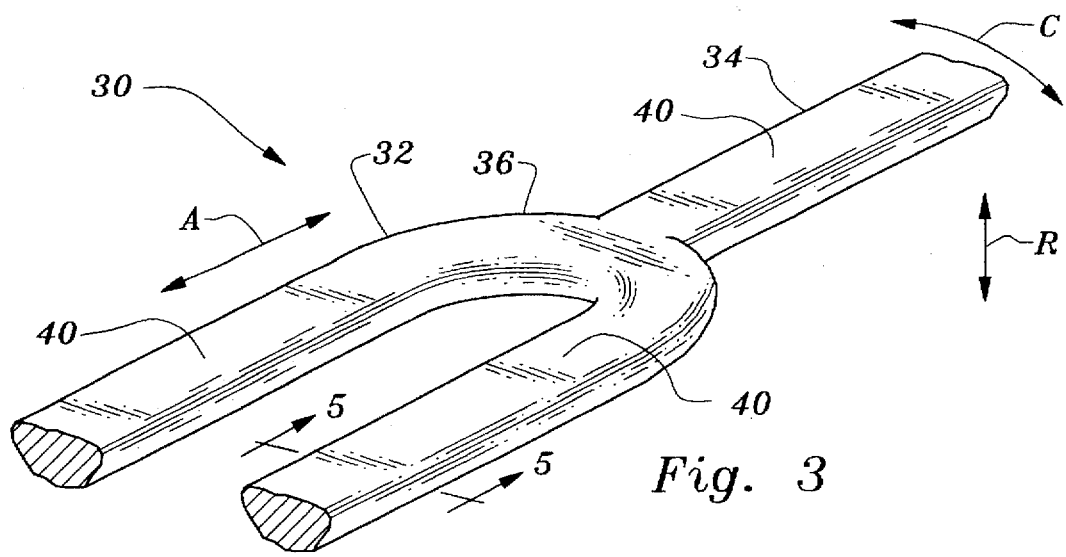
Fig. 3
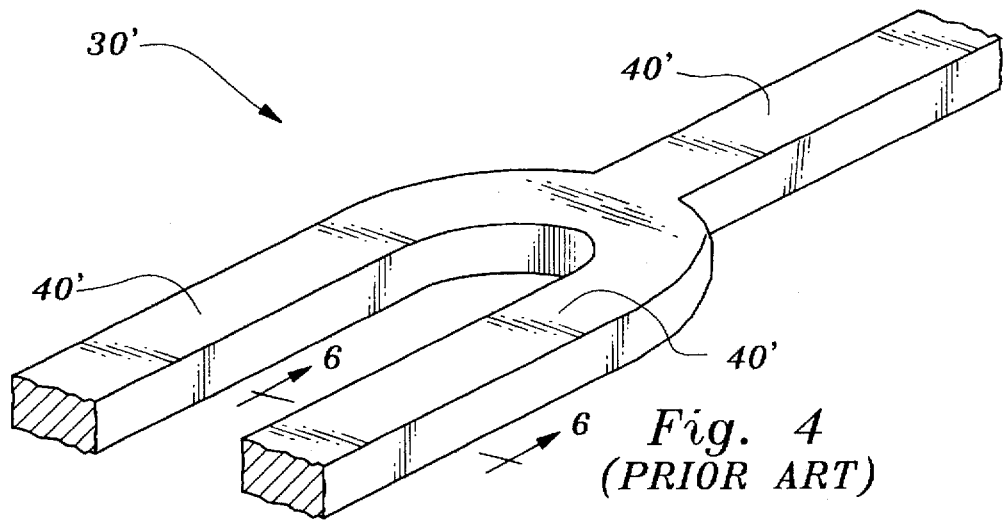
Fig. 4 (PRIOR ART)
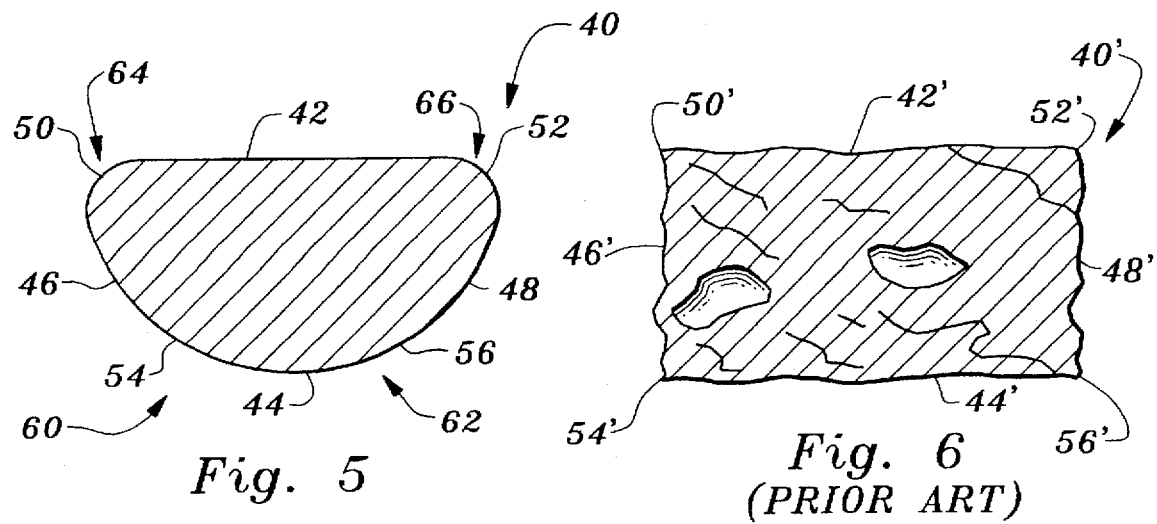
Fig. 5
Fig. 6 (PRIOR ART)

SURGICAL STENT HAVING A STREAMLINED CONTOUR

FIELD OF THE INVENTION

The following invention relates to surgical stents of a generally tubular configuration which can be surgically implanted into a body lumen, such as an artery, and be radially expanded to support the lumen. More specifically, this invention relates to radially expandable surgical stents which exhibit an inner surface which has a streamlined contour and a finely polished surface to minimize disruption of bodily fluid flow through the lumen.

BACKGROUND OF THE INVENTION

Surgical stents have long been known which can be surgically implanted into a body lumen, such as an artery, to reinforce, support, repair or otherwise enhance the performance of the lumen. For instance, in cardiovascular surgery it is often desirable to place a stent in the coronary artery at a location where the artery is damaged or is susceptible to collapse. The stent, once in place, reinforces that portion of the artery allowing normal blood flow to occur through the artery. One form of stent which is particularly desirable for implantation in arteries and other body lumens is a tubular stent which is formed as a complete tubular cylinder and can be radially expanded from a first smaller diameter to a second larger diameter. Such radially expandable stents can be inserted into the artery by being located on a catheter and fed internally through the arterial pathways of the patient until the unexpanded stent is located where desired. The catheter is fitted with a balloon or other expansion mechanism which exerts a radial pressure outward on the stent causing the stent to expand radially to a larger diameter. Such expandable stents exhibit sufficient rigidity after being expanded that they will remain expanded after the catheter has been removed.

Radially expandable stents come in a variety of different configurations to provide optimal performance to various different particular circumstances. For instance, the patents to Lau (U.S. Pat. Nos. 5,514,154, 5,421,955, and 5,242,399), Baracci (U.S. Pat. No. 5,531,741), Gaterud (U.S. Pat. No. 5,522,882), Gianturco (U.S. Pat. Nos. 5,507,771 and 5,314,444), Termin (U.S. Pat. No. 5,496,277), Lane (U.S. Pat. No. 5,494,029), Maeda (U.S. Pat. No. 5,507,767), Marin (U.S. Pat. No. 5,443,477), Khosravi (U.S. Pat. No. 5,441,515), Jessen (U.S. Pat. No. 5,425,739), Hickle (U.S. Pat. No. 5,139,480), Schatz (U.S. Pat. No. 5,195,984), Fordenbacher (U.S. Pat. No. 5,549,662) and Wiktor (U.S. Pat. No. 5,133,732), each include some form of radially expandable stent for implantation into a body lumen.

Some problems which have been exhibited by prior art stents include that the inner and outer surfaces of the stents are not sufficiently streamlined or finely enough polished to prevent certain medical complications. For instance, thrombus, a phenomenon where a fibrous clot forms within cracks and other irregularities in the surface finish of an implanted object (such as a stent), is enhanced when the surfaces of the stent are not finely polished. Additionally, when the inner surface of the stent is substantially planar and has abrupt edges along borders thereof, turbulence is introduced into the blood. When a stent having such an abrupt edge is implanted into an artery, plaque and other deposits are provided with a site for collection and potential narrowing of the arteries and restriction of blood flow this plaque buildup adjacent an implanted object (such as a stent) is referred to as "restenosis."

While many prior art stents do exhibit polished surfaces, they are typically not sufficiently finely polished, especially on tubularly formed stents having smaller diameters, to prevent restenosis and to thrombus adjacent the stent after the stent is implanted into the artery. Even when finely polished, such prior art stents lack a streamlined contour to minimize disruption of bodily fluid flow through the lumen and to further discourage restenosis surrounding the stent.

Accordingly, a need exists for a radially expandable surgical stent which exhibits a particular streamlined contour and smoothness which minimizes negative medical complications after the surgical stent is implanted within a body lumen.

SUMMARY OF THE INVENTION

The radially expandable surgical stent of this invention exhibits an overall tubular cylindrical hollow seamless contour which can feature any of a variety of different arrangements for individual elements and segments forming the stent. The various different segments of the stent have a generally elongate, substantially constant cross-sectional contour which can either be oriented to extend axially, circumferentially, or some combination thereof, with each segment located between an inner diameter of the stent and an outer diameter of the stent. Each segment includes an outer surface coextensive with the outer diameter of the stent and an inner surface coextensive with the inner diameter of the stent. Each segment also includes lateral surfaces extending between the inner surface and the outer surface which can either be a leading surface on an upstream side of the segment, a trailing surface on a downstream side of the segment, or a lateral surface generally aligned axially with the stent.

The inner surface of each segment of the stent is extensively streamlined to minimize disruption of bodily fluid flow through the body lumen. Specifically, the inner surface includes an inner leading edge and an inner trailing edge bordering the inner surface. Each inner edge is defined by an inner curve having a relatively large radius of curvature when compared to the radii of curvature exhibited by outer edges adjacent the outer surface of each stent segment. Because the inner edges have a large radius of curvature, they do not present any abrupt transition in flow for bodily fluids passing over the inner surface of the stent segment, particularly when the stent segment is aligned circumferentially with bodily fluid flow passing adjacent the inner surface from a leading inner edge to a trailing inner edge.

The surfaces of each stent segment are configured to have a surface finish which is free from abrupt transitions and irregularities, such as prominences extending more than five micro inches above adjacent portions of the surrounding surface. Smooth flow of blood or other bodily fluids over the surfaces of the stent can thus be preserved and a risk of medical complications such as restenosis and thrombus can be minimized.

OBJECTS OF THE INVENTION

Accordingly, a primary object of the present invention is to provide a radially expandable surgical stent which has a generally cylindrical contour with an inner diameter defined by inner surfaces of segments forming the stent and an outer diameter defined by outer surfaces of the segments forming the stent, the inner surfaces having a streamlined contour to minimize disruption of blood flow passing over segments of the stent when the stent is implanted within an artery or other body lumen.

Another object of the present invention is to provide a surgical stent which minimizes medical complications such as restenosis and thrombus adjacent the stent.

Another object of the present invention is to provide a radially expandable surgical stent which has a finish smoothness which minimizes medical complications such as restenosis and thrombus adjacent the stent when the stent is implanted within an artery or other body lumen.

Another object of the present invention is to provide a surgical stent which can support a body lumen while minimizing disruption of flow of bodily fluids through the lumen.

Another object of the present invention is to provide a surgical stent which is reversible and can be implanted in two distinct orientations rotated 180° from each other without altering performance of the surgical stent.

Another object of the present invention is to provide a surgical stent which features an inner surface which has edges with greater radii of curvature than radii of curvature of outer edges bordering an outer surface of segments of the stent, such that disruption to blood flow within a body lumen in which the stent is implanted is minimized and the outer surface of the stent is securely held adjacent a wall of the lumen.

Other further objects of the present invention will become apparent from a careful reading of the included description and claims and from a review of the drawing figures.

BRIEF DESCRIPTION OF THE DRAWINGS

FIG. 3 is a perspective view of a stent segment representative of stent segments of another alternative stent to that which is shown in FIG. 1.

FIG. 4 is a perspective view of a stent segment similar to that which is shown in FIG. 3, but exhibiting a contour found in many representative prior art stents.

FIG. 5 is a full sectional view taken along line 5—5 of FIG. 1, 2 or 3 revealing a specific contour of surfaces of the stem segments according to this invention.

FIG. 6 is a full sectional view taken along line 6—6 of FIG. 4 revealing details of a typical contour of a representative prior art stent segment.

DESCRIPTION OF THE PREFERRED EMBODIMENT

Figure 8:
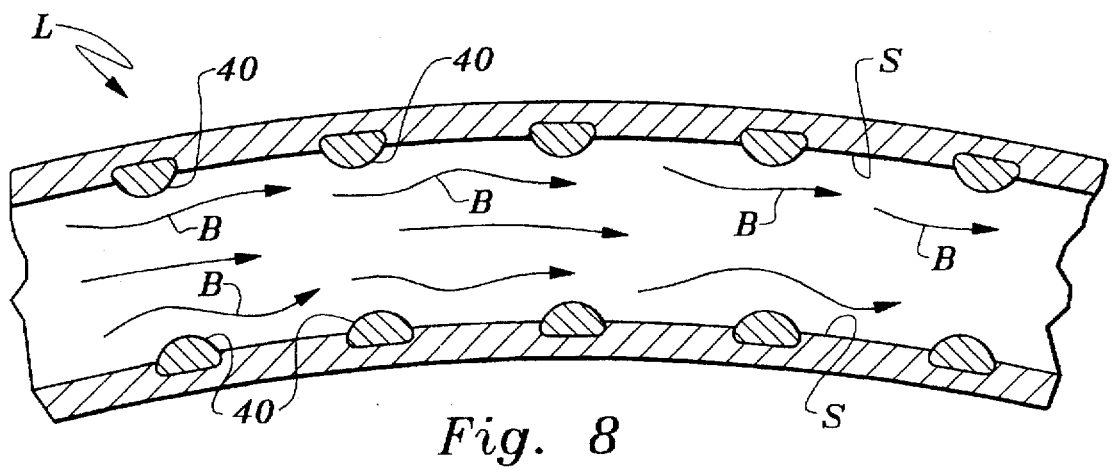
FIG. 8 is a full sectional view of a stent featuring the preferred cross-sectional contour of this invention and shown implanted within a lumen, such as an artery.

Referring to the drawings, wherein like reference numerals represent like parts throughout the various drawing figures, reference numeral 10 is directed to a radially expandable surgical stent (FIG. 1) for implantation within a body lumen L (FIG. 8) and to which the specific contour of this invention can be applied. A stent such as the surgical stent 10 is formed from multiple stent segments, such as the stent segments 40 (FIG. 3) which feature a particular cross-sectional contour (FIG. 5). This contour is characterized by having an inner surface 44 which is dissimilar to an outer surface 42 such that the inner surface 44 is streamlined to minimize disruption of bodily fluid flow passing over the inner surface 44 when the stent 10 is implanted within a body lumen L (FIG. 8).

In essence, and with particular reference to FIG. 5, the cross-sectional contour of each stent segment 40 is described. Each stent segment 40 is an elongate construct of substantially constant cross-sectional generally rectangular form, having an outer surface 42 opposite an inner surface 44. Two lateral side surfaces including a leading surface 46 and a trailing surface 48 extend between the inner surface 44 and the outer surface 42. The inner surface 44 is provided with an inner leading edge 54 and an inner trailing edge 56 which are defined by an inner leading curve 60 and an inner trailing curve 62, respectively, with sufficiently high radii of curvature 70, 72 (FIG. 7) that the inner surface 44 is highly streamlined between the inner leading edge 54 and the inner trailing edge 56.

The outer surface 42 extends between two side edges including an outer leading edge 50 and an outer trailing edge 52. The outer leading edge 50 is defined by an outer leading curve 64 and the outer trailing edge 52 is defined by an inner trailing curve 62. The inner leading curve 60 and inner trailing curve 62 are have radii of curvature 74, 76 (FIG. 7) which are less than the radii of curvature 70, 72 of the inner leading curve 60 and the inner trailing curve 62 (FIG. 5). The stent segment 40 thus has a contour which presents a highly streamlined gradually curving surface for passage of bodily fluid B (FIG. 8) there over and the outer surface 42 presents a more abrupt contour for secure positioning adjacent an inner surface S of the body lumen L (FIG. 8).

Figure 1:
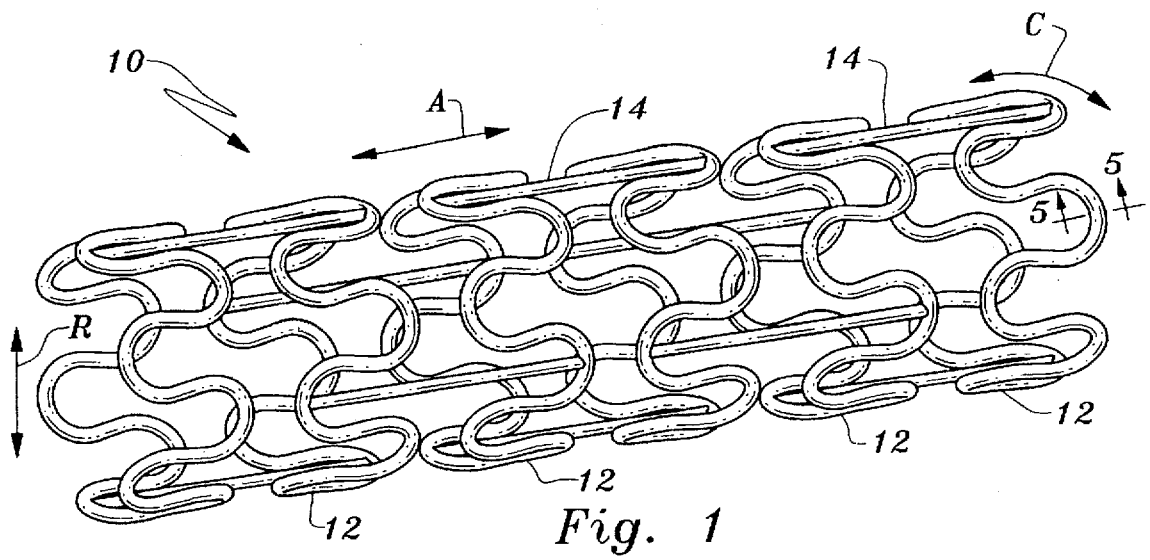
FIG. 1 is a perspective view of a radially expandable surgical stent featuring the streamlined contour of this invention.
Figure 2:
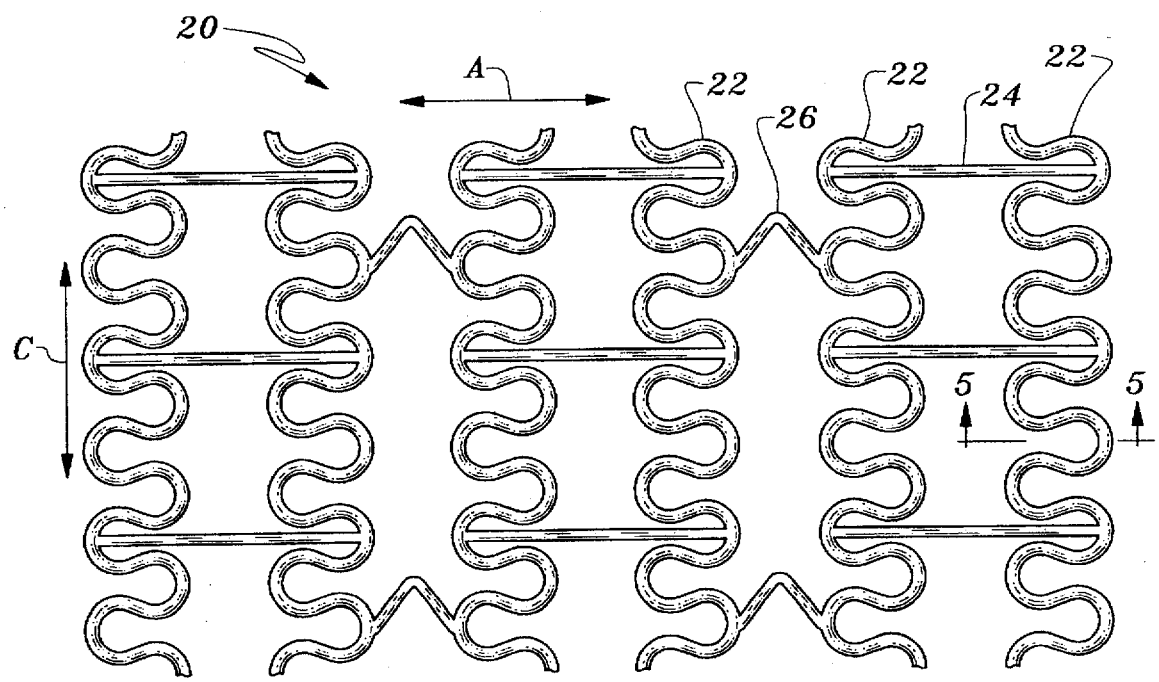
FIG. 2 is a cylindrical projection of an alternative stent of that which is shown in FIG. 1 which also features the streamlined contour of this invention.

More specifically, and with particular reference to FIGS. 1–3, details of the radially expandable surgical stent 10 and its alternatives 20, 30 are described. The contour featured by this invention (FIG. 5) can be beneficially incorporated into surgical stents of a variety of different configurations, and stents of a variety of different materials, including radially expandable metallic stents formed of surgical steel, nickel titanium, polyhydrocarbons, metallic alloys or other implantable materials. For instance, the radially expandable surgical stent 10 (FIG. 1) can exhibit streamlined segments having the contour of the stent segment 40 shown in FIG. 5, as represented by section lines 5—5.

The surgical stent 10 is formed from a series of separate circumferential elements 12 passing circumferentially, along arrow C, entirely around the cylindrical radially expandable surgical stent 10, preferably in a seamless manner. Axial elements 14, extending along arrow A, are affixed between adjacent circumferential elements 12 to tie the circumferential elements 12 together and form the stent 10 as a single tubular unit. When the stent 10 is configured with the streamlined contour of this invention (FIG. 5), the inner surface 44 faces radially inward toward a central axis of the stent 10 and the outer surface 42 faces radially outward (along arrow R) away from a central axis of the stent 10. With the streamlined contour of the stent segment 40 shown in FIG. 5, the surgical stent 10 can beneficially support a body lumen L (FIG. 8) with individual stent segments 40 having a minimal effect on blood/fluid flow B through a body lumen L, such as an artery.

To further exhibit the ability of the streamlined contour of the stent segment 40 (FIG. 5) of this invention to be incorporated into stents of different configurations, an alternative stent 20 is shown (FIG. 2) exhibiting the unique contour of this invention. In the alternative stent 20. (FIG. 2) a series of serpentine circumferential elements 22 are oriented circumferentially surrounding the alternative stent 20, along arrow C. Axial elements 24 are oriented axially, aligned with arrow A, and tie adjacent circumferential elements 22 together. Angled elements 26 replace axial elements 24 between some pairs of circumferential elements 22 to provide additional flexibility to the alternative stent 20, as shown by section line 5—5 of FIG. 2. The streamlined contour of the stent segment 40 of FIG. 5 can be incorporated into the alternative stent 20 to provide the benefits of the contour of the stent segment 40 to the alternative stent 20 in a manner similar to that described above with respect to the surgical stent 10 of FIG. 1.

Another alternative stent 30 (FIG. 3) is designed with stent segments 40 including circumferential elements 32 extending in a serpentine pattern circumferentially, along arrow C around the stent 30 with axial elements 34 joining adjacent circumferential elements 32. In the alternative stent 30, the axial element 34 joins to the circumferential element 32 adjacent a crest 36 in the circumferential element 32. As shown in FIG. 4, such stents, represented by reference numeral 30' are common in the prior art which feature stent segments 40' but which lack the particular contour of the stent segment 40 of this invention.

The circumferential elements 32 of the alternative stent 30 and the axial elements 34 of the alternative stent 30 can similarly be provided with the unique contour exhibited in FIG. 5, as represented by section line 5—5 shown in FIG. 3. However, when the stent segment 40 is oriented axially along arrow A, blood/body fluid flow B over the inner surface 44 of the stent segment 40 is rotated 90° when compared to the orientation of the stent segment 40 and inner surface 44 when the circumferential element 32 in which the inner surface 44 is located extends circumferentially, as shown in FIGS. 1 and 2 by section lines 5—5.

Figure 7:
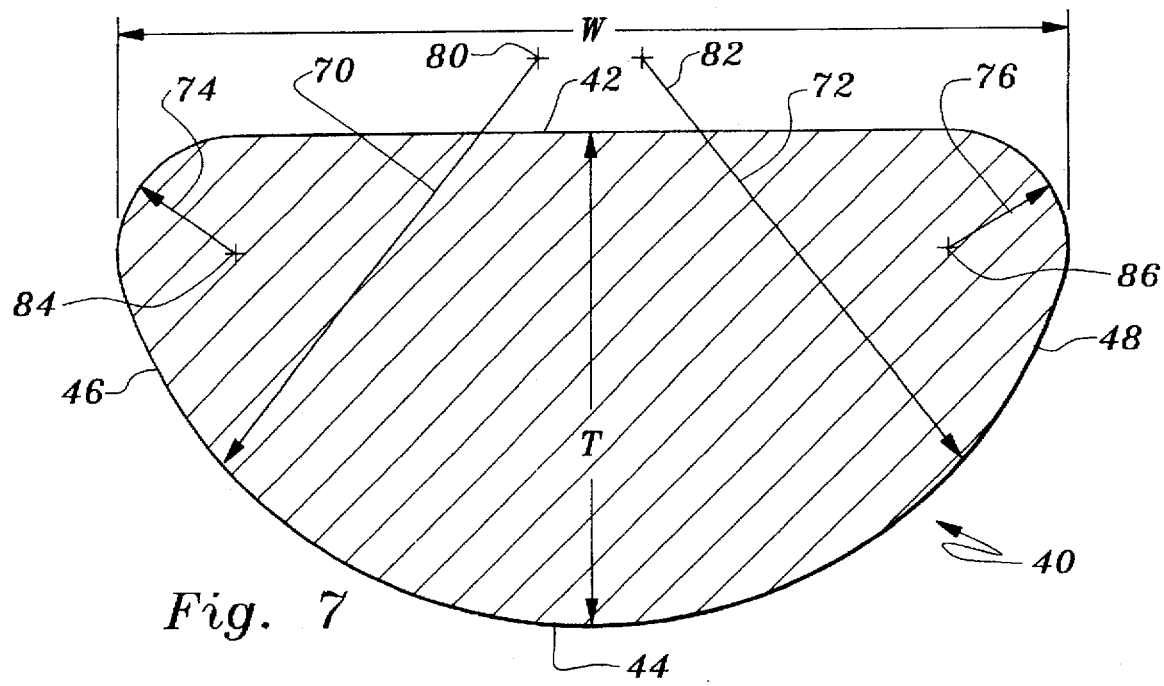
FIG. 7 is a full sectional view similar to that which is shown in FIG. 5 and further revealing details of the contour of segments forming a stent according to this invention.

With particular reference to FIGS. 5 and 7, details of the particular contour of the stent segment 40 are described. The stent segment 40 is an elongate substantially rigid construct having a substantially constant cross-section as represented in FIG. 5. This cross-section exhibits a contour which is streamlined to optimize blood/body fluid flow B (FIG. 8) over the inner surface 44 of the stent segment 40. The stent segment 40 is somewhat rectangular in cross-section except that corners of the cross-section of the stent segment 40 are curved to varying degrees, altering the cross-sectional contour of the stent segment 40 away from what would be a more particularly rectangular contour. Hence, an outer surface 42 is presented forming one surface of the stent segment 40, substantially coextensive with an outer diameter of the surgical stent 10, or alternative stents 20, 30. An inner surface 44 is oriented opposite the outer surface 42. The inner surface 42 is coextensive with an inner diameter of the stents 10, 20, 30 and is roughly parallel to the outer surface 42. Because the inner surface 44 is highly rounded the inner surface 44 is actually only parallel to the outer surface 42 adjacent a middle region of the inner surface 44.

Two lateral side surfaces 46, 48 extend between the inner surface 44 and the outer surface 42 and form the remaining two sides of the somewhat rectangular stent segment 40. The lateral side surfaces 46, 48 include a leading surface 46 and a trailing surface 48. While the leading surface 46 is oriented facing upstream much of the time when a stent such as the surgical stent 10, fitted with the stent segment 40 of this invention is implanted within a body lumen L (FIG. 8), it is also possible that the leading surface 46 can in fact be oriented parallel to a direction of flow of blood/fluid flow B within a body lumen L if the stent segment 40 is oriented axially, such as is shown in FIG. 3 for the alternative stent 30. Similarly, the trailing surface 48, while often facing downstream when incorporated into a stent 10 implanted within a body lumen L, can have other orientations when incorporated into stents of different configurations. Hence, the terminology "leading" and "trailing" is not intended to limit the orientation in which these lateral side surfaces 46, 48 can be oriented.

The outer surface 42 extends between an outer leading edge 50 and an outer trailing edge 52. The outer leading edge 50 defines a transition between the outer surface 42 and the leading surface 46. The outer trailing edge 52 defines a transition between the outer surface 42 and the trailing surface 48. The outer surface 42 is preferably substantially planar between the outer leading edge 50 and the outer trailing edge 52.

The inner surface 44 extends between an inner leading edge 54 and an inner trailing edge 56. The inner surface 44 preferably has a small substantially planar area at a mid point between the inner leading edge 54 and the inner trailing edge 56 which is substantially parallel to the outer surface 42. A thickness T of the stent segment 40 is defined by the distance between the outer surface 42 and the inner surface 44. Alternatively, the inner surface 44 can lack any planar region but rather curve continuously between the inner leading edge 54 and the inner trailing edge 56 with the thickness T of the stent segment 40 defined by a distance between the outer surface 42 and a mid point in the inner surface 44 between the inner leading edge 54 and the inner trailing edge 56, where the thickness T of the stent segment 40 is at a maximum.

The leading surface 46 and trailing surface 48 are preferably mirror images of each other and extend between the inner surface 44 and outer surface 42, smoothly joining the inner surface 44 with the outer surface 42 without any abrupt transitions between the outer surface 42 and the inner surface 44. The leading surface 46 and trailing surface 48 preferably do not have any planar regions thereon, but rather continuously curve between the inner surface 44 and the outer surface 42. The stent segment 40 thus has each surface 42, 44, 46, 48 joining to adjacent surfaces through edges 50, 52, 54, 56, somewhat analogous to the four corners of a rectangle.

The inner leading edge 54 has a contour specifically defined by an inner leading curve 60 extending from the leading surface 46 to the inner surface 44. Similarly, the inner trailing edge 56 has its contour defined by an inner trailing curve 62 extending from the inner surface 44 to the trailing surface 48. The inner curves 60, 62 are free of abrupt transitions, but rather provide a smooth transition between the lateral side surfaces 46, 48 and the inner surface 44. Preferably, the inner curves 60, 62 are exact mirror images of each other.

In defining the exact contour of the inner curves 60, 62 each curve 60, 62 is provided with a radius of curvature including the inner leading radius of curvature 70 and the inner trailing radius of curvature 72. Each inner radius of curvature 70, 72 extends from a center of curvature such as the inner leading center of curvature 80 or the inner trailing center of curvature 82. The exact radii of curvature for the inner curves 60, 62 and the centers of curvature 80, 82 for the inner curves 60, 62 can be varied somewhat to conform to the particular design parameters of the application in which the stent segment 40 is to be utilized.

Factors to consider in the design of the contour for the inner curves 60, 62 and the selection of the radii of curvature 70, 72 and the centers of curvature 80, 82 include the desired coefficient of drag between the stent segment 40 and the fluid passing adjacent thereto, the viscosity of the fluid intended to be passing adjacent thereto, the diameter of the stent 10 in which the stent segment 40 is located, the extent to which the stent 10 is expected to embed itself into inner surfaces S of the body lumen L in which the stent 10 is implanted (FIG. 8), and other design parameters relevant to the particular application in which the stent 10 is to be utilized. It is considered preferable for many applications to form the radii of curvature 70, 72 to have a size greater than the size of the thickness T of the stent segment 40, such that the centers of curvature 80, 82 are located above the outer surface 42 of the stent segment 40. For instance, when a thickness T of the stent segment 40 is 0.003 inches, radii of curvature 70, 72 for the inner curves 60, 62 can be 0.004 inches or greater.

While useful in illustrating the specific contour of the inner curves 60, 62, it is not required that the inner curves 60, 62 have constant radii of curvature 70, 72 or a constant position for the centers of curvature 80, 82. Rather, it is preferable that the inner curves 60, 62 in fact be a "French" curve without a constant radius of curvature or an exact fixed position for a center of curvature. When the inner curves 60, 62 exhibit such a French curve contour, the radii of curvature 70, 72 are initially smaller adjacent the lateral side surfaces 46, 48 and the centers of curvature 80, 82 are initially closer to the inner surface 44. As the curves 60, 62 extend away from the lateral side surfaces 46, 48 and toward a middle of the inner surface 44, the radii of curvature 70, 72 increase and the position of the centers of curvature 80, 82 move away from the inner surface 44. Preferably, the resulting contours of the inner curves 60, 62 are somewhat analogous to streamlined surfaces found effective in minimizing coefficients of drag.

The outer leading edge 50 and outer trailing edge 52 of the outer surface 42 are defined by an outer leading curve 64 and an outer trailing curve 66, respectively. The outer curves 64, 66 are similar to each other but contrasted with the inner curves 60, 62 adjacent the inner surface 44. Specifically, the outer curves 64, 66 are defined by an outer leading radius of curvature 76 and an outer trailing radius of curvature 78 distinct from the radii of curvature 70, 72 of the inner curves 60, 62. Additionally, the outer curves 64, 66 are centered upon an outer leading center of curvature 86 and an outer trailing center of curvature 88 which are closer to the outer curves 66, 68 than is the case with the inner curves 60, 62.

Preferably, the outer curves 64, 66 are similar in contour to each other and exhibit fixed radii of curvature 74, 76 which are less than half of a size of the thickness T of the stent segment 40. Unlike the inner curves 60, 62, the outer curves 64, 66 preferably exhibit radii of curvature 74, 76 which are constant in size and with fixed centers of curvature 84, 86.

Because the outer curves 64, 66 are configured to rest against the inner surface S of the lumen L (FIG. 8), such as an artery, streamlining of the outer curves 64, 66 is not a priority. Rather, it is beneficial to provide the outer curves 64, 66 with a sufficiently smooth surface that no sharp corner is presented at the outer leading edge 50 and outer trailing edge 52 which could irritate the tissues forming the inner surface S of the lumen L and potentially stimulate thrombus or damage to the inner surface S of the lumen L. By maintaining the radii of curvature 74, 76 of the outer curve 64, 66 below half of the thickness T of the stent segment 40, the outer curves 64, 66 are sufficiently abrupt to allow the outer surface 42 to securely engage the inner surface S of the lumen L and resist displacement of the stent 10 longitudinally along the lumen L away from the stent's original and desired position.

The lateral side surfaces 46, 48 are preferably spaced apart by a width W which is defined as the dimension of greatest distance between the leading surface 46 and the trailing surface 48 of the stent segment 40. This maximum width W point also defines a transition where the contour of the outer curves 64, 66 transition to the contours of the inner curves 60, 62 for embodiments where no planar leading surface 46 or trailing surface 48 is provided. In one form of the invention, the outer curves 64, 66 can gradually transition into the inner curves 60, 62 by having the radii of curvature 70, 72 of the inner curves 60, 62 match the radii of curvature 74, 76 of the outer curves 64, 66 adjacent this maximum width W point. The radii of curvature 70, 72 of the inner curve 60, 62 would then begin to increase as the inner curves 60, 62 continue toward a middle of the inner surface 44. Simultaneously, the centers of curvature 80, 82 would begin to migrate from the location of the centers of curvature 84, 86 of the outer curves 64, 66 to their positions above the outer surface 42.

Figure 9:
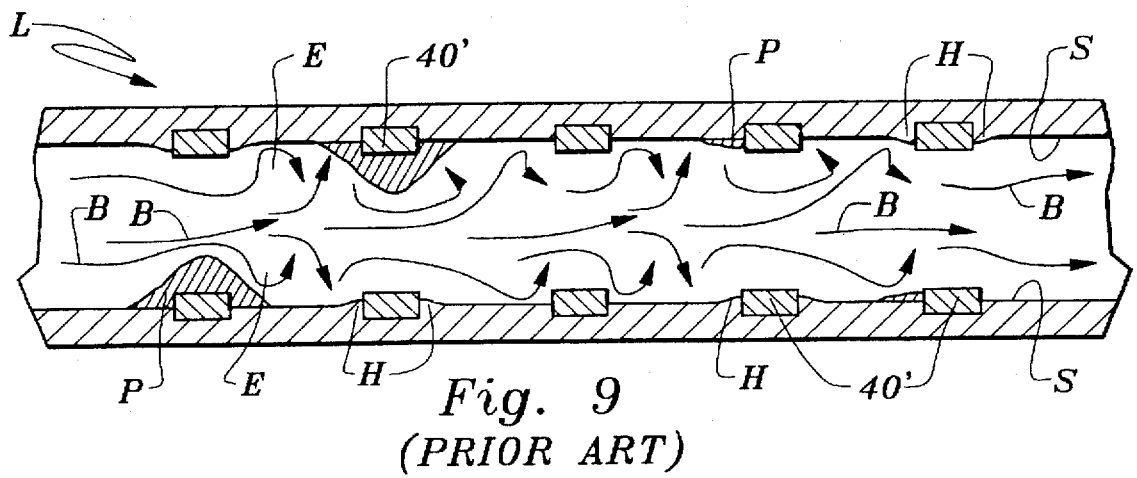
FIG. 9 is a full sectional view of a lumen, such as an artery, with a prior art stent implanted therein.

In addition to the particular contour of the curves 60, 62, 64, 66 forming the stent segment 40, it is a beneficial feature of this invention that a finish of the surfaces 42, 44, 46, 48 be particularly smooth to minimize prominences which could cause irritation for tissues forming the inner surface S of the lumen L or which could disrupt blood/fluid flow B (FIG. 8) or provide sites at which plaque P, leading to restenosis or thrombus H could occur, as shown in FIG. 9. Specifically, and as shown in FIGS. 4–6, prior art stent segments 40' are typically substantially rectangular in cross-section with a substantially planar outer surface 42' parallel to and spaced from a substantially planar inner surface 44'. A leading surface 46' is substantially planar and parallel to and spaced from a substantially planar trailing surface 48'. Edges 50', 52', 54', 56' generally correspond to edges 50, 52, 54, 56 in the stent segment 40 of this invention.

Such prior art stent segments 40' not only lack the particular streamlining and contouring discussed above with regard to the stent segment 40, but additionally exhibit a relatively high degree of irregularities in their surface finish, lacking a smoothness desirable for optimal performance of the stent 10. Specifically, during manufacture, many stent segments 40 get etched and pitted by corrosive materials utilized to form and polish the stents (FIG. 6). While such irregularities are typically microscopic and only visible with image magnifying equipment, the surfaces are sufficiently irregular (i.e. irregularities larger than five micro inches) that they cause irritation to tissues forming the inner surfaces S of lumens L in which the stents are implanted (FIG. 9). Such irritation can lead to thrombus H, a phenomena where tissues surrounding an implant, such as a stent, are stimulated to grow into crevices and cracks in the implant and plaque P buildup (restenosis) tending to clog the lumen L or otherwise cause irritation to the lumen L. Accordingly, it is a desirable feature of this invention that the surface finish have a smoothness which eliminates prominences greater than five micro inches and preferably less than two to three micro inches.

In use and operation, when a stent 10 featuring stent segments 40 of this invention is implanted into a lumen L (FIG. 8) with the stent segments 40 embedding slightly into the inner surface S of the lumen L and supporting the lumen L, blood/fluid flow B is only slightly disrupted and restenosis and plaque buildup is minimized. When prior art stents are implanted (FIG. 9) stent segments 40 having more abrupt contours cause disruption in the blood/fluid flow B producing eddies E which further disrupt blood/fluid flow B and encourage the formation of plaque P, leading to restenosis, along the inner surface S at various locations along the inner surface S. Thrombus H is also stimulated by irregularities in surface finish exhibited by stent segments 40' of prior art stents.

Because the leading curves 60, 64 generally matching the contour of the trailing curves 62, 66 of each stent segment 40, the stent 10 featuring the stent segment 40 can be reversed 180° with similar function in either orientation. Alternatively, should maximum streamlining of the stent segment 40 be desired, the inner surface 44 can be provided with a more airfoil-like asymmetrical contour which does not provide the leading surface 46 and trailing surface 48 as mirror images of each other, but rather provides the leading surface 46 with a smaller radius of curvature and the trailing surface 48 with a larger radius of curvature or a tapering gradual slope, somewhat analogous to that of a tear drop in cross-section. Such an asymmetrical surgical stent would necessarily only benefit from its form when implanted in a particular direction with regard to blood/fluid flow B through the lumen L.

Having thus described the invention, it should be apparent that numerous modifications to the specific details described herein could be resorted to without departing from the scope of this invention as claimed herein. Additionally, the particular details provided in this description are not provided to limit the interpretation of the claims to this invention, but rather are presented by way of example and to supply an enabling disclosure and best mode for practicing this invention.

What is claimed is:

1. A radially expandable surgical stent for implanting into a body lumen to improve the function of the body lumen, the stent comprising in combination:

a plurality of segments joined together to form a hollow generally cylindrical stent, each said segment having an inner surface defining part of an inner diameter of said stent and an outer surface defining part of an outer diameter of said stent;

said inner surface bordered by inner curved edges;

said outer surface bordered by outer curved edges; and said inner edges having a greater radius of curvature than said outer edges, such that said inner surface is streamlined to facilitate smooth passage of body fluids through the lumen in which said stent is implanted.

2. The stent of claim 1 wherein said inner edges include an inner leading curve and an inner trailing curve, said inner leading curve adjacent a leading surface of said segment between said inner surface and said outer surface, said inner trailing curve between said inner surface and a trailing surface between said inner surface and said outer surface of said segment and opposite said leading surface, said inner leading curve having an inner leading radius of curvature substantially equal to an inner trailing radius of curvature of said inner trailing curve, such that said inner edges are substantially mirror images of each other and said stent is reversible.

3. The stent of claim 2 wherein said outer edges include an outer leading curve and an outer trailing curve, said outer leading curve having an outer leading radius of curvature and said outer trailing curve having an outer trailing radius of curvature, both said inner leading radius of curvature and said inner trailing radius of curvature greater than said outer leading radius of curvature and said outer trailing radius of curvature.

4. The stent of claim 3 wherein said inner leading radius of curvature is greater than twice a size of said outer leading radius of curvature.

5. The stent of claim 1 wherein said segments of said stent are formed from a metallic material.

6. The stent of claim 1 wherein said inner surface and said outer surface of said stent are free from corrosion induced pitting resulting from exposure of said stent to corrosive materials.

7. The stent of claim 1 wherein said inner surface of said stent exhibits a finish smoothness having no deformations extending more than five micro inches above surrounding portions of said inner surface.

8. The stent of claim 1 wherein said inner leading radius of curvature has a size greater than a size of a thickness of said segment between said inner surface and said outer surface.

9. A stent for surgical implantation into a body lumen which minimizes disruption of flow of bodily fluids through the body lumen and resists restenosis surrounding said stent, said stent comprising in combination:

a plurality of segments joined together to form a hollow generally cylindrical stent, each said segment having an inner surface defining part of an inner diameter of said stent and an outer surface defining part of an outer diameter of said stent;

said inner surface and said outer surface extending between a leading surface and a trailing surface, said leading surface located upstream from said trailing surface when said stent is located within the body lumen;

an inner leading edge located between said leading surface and said inner surface;

an outer leading edge located between said leading surface and said outer surface; and said inner leading edge having an inner leading curve which is more gradual than an outer leading curve of said outer leading edge.

10. The stent of claim 9 wherein said inner surface, said leading surface and said trailing surface have a finish smoothness which is free of deformations extending more than five micro inches above surrounding portions of said inner surface, said leading surface and said trailing surface.

11. The stent of claim 10 wherein said stent is formed from a metallic material taken from the group of materials including stainless steel, nickel titanium, polyhydrocarbons and implantable materials and alloys.

12. The stent of claim 11 wherein said inner surface, said outer surface, said leading surface and said trailing surface are free from pitting induced by exposure of said stent to corrosive materials.

13. The stent of claim 12 wherein said segments of said stent are joined together in a manner allowing a diameter of said stent to be expanded.

14. The stent of claim 13 wherein said inner trailing edge has an inner trailing curve which is substantially a mirror image of said inner leading curve of said inner leading edge, such that said inner leading edge and said inner trailing edge are mirror images of each other and said stent is reversible.

15. A surgical stent for implantation into a body lumen, said stent having a substantially cylindrical contour and being radially expandable, the stent comprising in combination:

a plurality of circumferential elements, each circumferential element encircling said cylindrical contour of said stent;

at least two of said plurality of circumferential elements having an undulating form including at least one trough and at least one crest as said undulating circumferential elements circumscribe said cylindrical contour of said stent;

at least one axial element located between two adjacent said circumferential elements and attached to one of said adjacent circumferential elements at a first junction and to the other of said circumferential elements at a second junction;

each said element having an inner surface defining an inner diameter of said stent and an outer surface defining an outer diameter of said stent, wherein said inner surface is bordered by inner curved edges and said outer surface is bordered by outer curved edges, said inner edges having a greater radius of curvature than said outer edges; and said inner surface having a finish smoothness free of deformations extending more than five micro inches away from said inner surface, such that bodily fluid flow through a lumen fitted with said stent is only minimally disrupted by the presence of said stent within said lumen.

16. The surgical stent of claim 15 wherein said inner edges bordering said inner surface have contours which are mirror images of each other, such that said stent is reversible within the body lumen without altering resistance of said stent to bodily fluid flow when reversed within a lumen.

17. The surgical stent of claim 16 wherein said radius of curvature of said inner edges is greater than a thickness of said stent between said inner surface and said outer surface.

18. The surgical stent of claim 17 wherein said radius of curvature of said outer edges is less than said thickness of said stent.

19. The surgical stent of claim 18 wherein said radius of curvature of said inner edges is non-constant and has a maximum size which is greater than twice the size of said radius of curvature of said outer edges.

* * * * *